(12) United States Patent  (10) Patent No.: US 7,741,497 B2
Nishino et al.  (45) Date of Patent: Jun. 22, 2010

(54) PROCESSES FOR PREPARING ALKYL 3-(4-TETRAHYDROPYRANYL)-3-OXOPROPANOATE COMPOUND AND 4-ACYLTETRAHYDROPYRANE

(75) Inventors: Shigeyoshi Nishino, Ube (JP); Kenji Hirotsu, Ube (JP); Hidetaka Shima, Ube (JP); Keiji Iwamoto, Ube (JP); Takashi Harada, Ube (JP)

(73) Assignee: Ube Industries, Ltd., Ube-shi, Yamaguchi (JP)

( * ) Notice: Subject to any disclaimer, the term of this patent is extended or adjusted under 35 U.S.C. 154(b) by 1009 days.

(21) Appl. No.: 10/583,473

(22) PCT Filed: Dec. 17, 2004

(86) PCT No.: PCT/JP2004/018938

§ 371 (c)(1),
(2), (4) Date: Jun. 19, 2006

(87) PCT Pub. No.: WO2005/058859

PCT Pub. Date: Jun. 30, 2005

(65) Prior Publication Data

US 2007/0043107 A1  Feb. 22, 2007

(30) Foreign Application Priority Data

Dec. 19, 2003 (JP) .............................. 2003-422054
Dec. 22, 2003 (JP) .............................. 2003-424232
Nov. 12, 2004 (JP) .............................. 2004-328356

(51) Int. Cl.
*C07D 309/06* (2006.01)
(52) U.S. Cl. ..................................................... 549/425
(58) Field of Classification Search .................. 549/425
See application file for complete search history.

(56) References Cited

U.S. PATENT DOCUMENTS 6,153,560 A  11/2000  Oberdorf et al.

FOREIGN PATENT DOCUMENTS

| JP | 2000-044515 A | 2/2000 |
| JP | 2000-506179 A | 5/2000 |
| JP | 2001-172274 | * 6/2001 |
| JP | 2001-172274 A | 6/2001 |
| WO | WO 97/33874 | 9/1997 |
| WO | WO-2006/013920 A1 | 2/2006 |

OTHER PUBLICATIONS

Vartanyan, R. S. et al., Sov.- Indiiskii Simp. Khim. Prir. Soedin., 5th, 1978, 16.
Evstigneeva, R. P. et al., Zhurnal Obschei Khimii, 1961, vol. 31, pp. 443 to 445.
Hudson, Boyd E., Jr. et al., Journal of the American Chemical Society, 1941, vol. 63, pp. 3163 to 3164.
Vartanyan, R. S. et al., Armyanskii Khimicheskii Zhurnal, 1980, vol. 33, No. 2, pp. 163 to 166.
The Supplemental European Search Report mailed on Jun. 22, 2009, which issued in Application No. EP-04807296.
Hahn et al., "Uber substituierte 4-Amino-piperidine," Helv Chim Acta, 26, pp. 1132-1143, 1943.
Stanfield et al., "Spiroaminobarbituric Acids. I." J.A.C.S., vol. 81, 1959, pp. 5167-5171.
Greenhow et al., "The Chemistry of Fluorene. Part I. Condensations with 9-Fluorenylsodium," J.C.S, 1951, pp. 2848-2851.

* cited by examiner

*Primary Examiner*—Bernard Dentz
(74) *Attorney, Agent, or Firm*—Birch, Stewart, Kolasch & Birch, LLP

(57) ABSTRACT

The present invention is to provide a process for preparing an alkyl 3-(4-tetrahydropyranyl)-3-oxopropanoate compound represented by the formula (1):

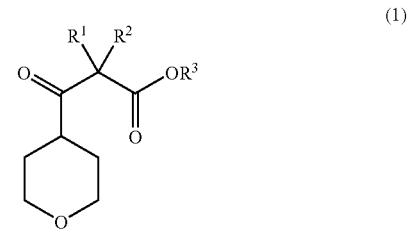

(1)

wherein $R^1$ and $R^2$ may be the same or different from each other, and represent a group which does not participate in the reaction, and $R^1$ and $R^2$ may be bonded to form a ring, and the ring may contain a hetero atom(s), and $R^3$ represents a hydrocarbon group,
which comprises reacting 4-acyltetrahydropyran represented by the formula (2):

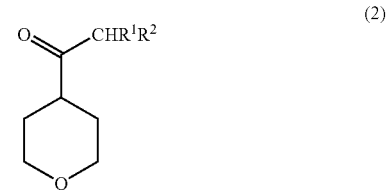

(2)

wherein $R^1$ and $R^2$ have the same meanings as defined above,
and a carbonic acid diester represented by the formula (3):

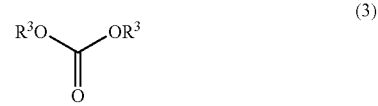

(3)

wherein $R^3$ has the same meanings as defined above, and two $R^3$s may be bonded to each other to form a ring,
in the presence of a base, and a process for preparing 4-acyltetrahydropyran.

13 Claims, No Drawings

PROCESSES FOR PREPARING ALKYL 3-(4-TETRAHYDROPYRANYL)-3-OXOPROPANOATE COMPOUND AND 4-ACYLTETRAHYDROPYRANE

TECHNICAL FIELD

The present invention relates to a process for preparing an alkyl 3-(4-tetrahydropyranyl)-3-oxopropanoate compound from a 4-acyltetrahydropyran and a process for preparing the 4-acyltetrahydropyran. The alkyl 3-(4-tetrahydropyranyl)-3-oxopropanoate compound and the 4-acyltetrahydropyran are useful compounds as starting materials or synthetic intermediates of medicines, agricultural chemicals, etc.

BACKGROUND ART

Heretofore, with regard to an alkyl 3-(4-tetrahydropyranyl)-3-oxopropanoate compound, there was a description of a name of methyl 4-tetrahydropyranoyl acetate, but there was no description on information about the synthetic method, physical properties, etc., so that it is doubtful whether the presence thereof could be confirmed or not at that time (for example, see Non-Patent literature 1).

Also, as a process for preparing 4-acyltetrahydropyran which is a starting compound of the present invention, there has been disclosed a method in which, for example, 2,2'-dichloroethyl ether and cyanoethyl acetate are reacted to synthesize ethyl 4-cyanotetrahydropyran-4-carboxylate, the resulting compound is hydrolyzed to prepare 4-cyanotetrahydropyran-4-carboxylic acid, then, the acid is heated under high temperature to synthesize 4-cyanotetrahydropyran, and further, a Grignard reagent is reacted thereto to prepare 4-acetyltetrahydropyran (for example, see Non-Patent literature 2). However, according to this method, multi-step reactions are required, and a Grignard reagent must be used so that the reaction operation or post-treatment becomes complicated, whereby it is not advantageous for an industrial process.

[Non-Patent literature 1] Tezisy Doki.-Sov.-Indiiskii Simp. Khim. Prir. Soedin. 5th, 1978, 16.

[Non-Patent literature 2] J. Am. Chem. Soc., 64, 1672 (1942)

DISCLOSURE OF THE INVENTION

Problems to be Solved by the Invention

An object of the present invention is to provide an industrially suitable process for preparing an alkyl 3-(4-tetrahydropyranyl)-3-oxopropanoate compound from 4-acyltetrahydropyran, which can prepare an alkyl 3-(4-tetrahydropyranyl)-3-oxopropanoate compound under mild conditions and simple and easy method.

Another object of the present invention is to solve the above-mentioned problems and to provide an industrially suitable process for preparing 4-acyltetrahydropyran which can prepare 4-acyltetrahydropyran under mild conditions without requiring any complicated operations and in high yield.

Means to Solve the Problems

The first invention of the present invention relates to a process for preparing an alkyl 3-(4-tetrahydro-pyranyl)-3-oxopropanoate compound represented by the formula (1):

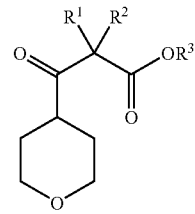

wherein $R^1$ and $R^2$ may be the same or different from each other, and represent a group which does not participate in the reaction, and $R^1$ and $R^2$ may be bonded to form a ring, and the ring may contain a hetero atom(s), and $R^3$ represents a hydrocarbon group, which comprises reacting 4-acyltetrahydropyran represented by the formula (2):

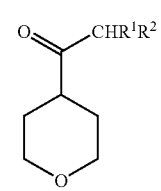

wherein $R^1$ and $R^2$ have the same meanings as defined above, and a carbonic acid diester represented by the formula (3):

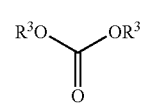

wherein $R^3$ has the same meaning as defined above, and two $R^3$s may be bonded to each other to form a ring, in the presence of a base.

The present invention also relates to an alkyl 3-(4-tetrahydropyranyl)-3-oxopropanoate compound represented by the formula (1):

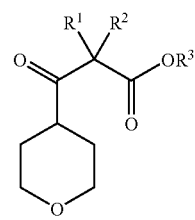

wherein $R^1$, $R^2$ and $R^3$ have the same meanings as defined above.

The second invention of the present invention relates to a process for preparing the 4-acyltetrahydropyran represented by the above-mentioned formula (2) which comprises subjecting a 4-acyl-4-alkoxycarbonyltetrahydropyran represented by the formula (4):

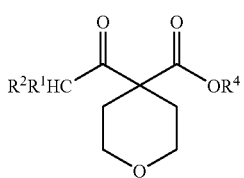

(4)

wherein R¹ and R² have the same meanings as defined above, and R⁴ represents an alkyl group, to decarboxylation in the presence of an acid.

The third invention of the present invention relates to the alkyl 3-(4-tetrahydropyranyl)-3-oxopropanoate compound represented by the above-mentioned formula (1).

The fourth invention of the present invention relates to a 4-propionyl-4-alkoxycarbonyltetrahydropyran represented by the formula (5):

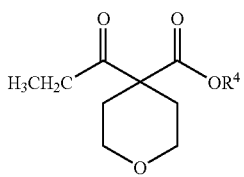

(5)

wherein R⁴ has the same meaning as defined above,
wherein CHR¹R² in the above-mentioned formula (4) is an ethyl group.

Effects of the Invention

According to the present invention, an industrially suitable process for preparing an alkyl 3-(4-tetrahydro-pyranyl)-3-oxopropanoate compound from 4-acyltetrahydropyran, which can prepare an alkyl 3-(4-tetrahydropyranyl)-3-oxopropanoate compound under mild conditions and simple and easy method can be provided.

Also, according to the present invention, an Industrially suitable process for preparing 4-acyltetrahydropyran which can prepare 4-acyltetrahydropyran under mild conditions without requiring any complicated operations and in high yield can be provided.

BEST MODE FOR CARRYING OUT THE INVENTION

The 4-acyltetrahydropyran to be used in the reaction of the first invention is represented by the above-mentioned formula (2). In the formula (2), R¹ and R² may be the same or different from each other, and represent a group which does not participate in the reaction, more specifically, there may be mentioned, for example, a hydrogen atom; a linear or branched alkyl group having 1 to 20 carbon atoms such as a methyl group, an ethyl group, a propyl group, a butyl group, a pentyl group, a hexyl group, a heptyl group, an octyl group, a nonyl group, a decyl group, a undecyl group, a dodecyl group, a tridecyl group, a tetradecyl group, a pentadecyl group, etc.; an aralkyl group such as a benzyl group, a phenethyl group, etc.; an aryl group in which 0 to 6 linear or branched alkyl group(s) having 1 to 6 carbon atoms is/are substituted to a phenyl group, a naphthyl group, an anthryl group, etc.; a linear or branched alkoxy group having 1 to 6 carbon atoms such as a methoxy group, an ethoxy group, a propoxy group, etc.; an aralkyloxy group in which a phenyl group, a naphthyl group, an anthryl group, etc. is bonded to a linear or branched acyloxy group having 1 to 6 carbon atoms; an aryloxy group having 6 to 20 carbon atoms such as a phenoxy group, etc.; an acyl group having 1 to 12 carbon atoms such as a formyl group, an acetyl group, a propionyl group, a benzoyl group, etc.; an acyloxy group having 1 to 6 carbon atoms such as a formyloxy group, an acetoxy group, a benzoyloxy group, etc.; and a halogen atom such as a fluorine atom, a chlorine atom, a bromine atom, an iodine atom, etc. Incidentally, these groups contain various kinds of isomers. Also, R¹ and R² may be bonded to each other to form a ring, and a hetero atom(s) may be contained in the ring. As the hetero atom(s), there may be mentioned, for example, an oxygen atom, a nitrogen atom and a sulfur atom, and those which contains 1 to 3 hetero atoms selected from the above may be mentioned. As the ring thus formed, there may be mentioned, for example, tetrahydro-furan, tetrahydropyran, tetrahydrothiofuran, tetrahydrothiopyran, etc.

The carbonic acid diester to be used in the reaction of the first invention is represented by the above-mentioned formula (3). In the formula (3), R³ is a hydrocarbon group, and there may be mentioned, for example, a linear or branched alkyl group having 1 to 12 carbon atoms such as a methyl group, an ethyl group, a propyl group, a butyl group, a pentyl group, a hexyl group, a heptyl group, an octyl group, a nonyl group, a decyl group, etc.; an aralkyl group having 7 to 20 carbon atoms such as a benzyl group, a phenethyl group, etc.; an aryl group having 6 to 20 carbon atoms such as a phenyl group, a naphthyl group, an anthryl group, etc., preferably a methyl group, an ethyl group. Incidentally, these groups contain various kinds of isomers. Also, two R³s may be bonded to each other to form a ring. Such a ring may be mentioned, for example, 1,3-dioxolane, 1,3-dioxetane, etc.

An amount of the carbonic acid diester to be used in the reaction of the first invention is preferably 1.0 to 50 mol, further preferably 2.0 to 20 mol based on 1 mol of the 4-acyltetrahydropyran.

The base to be used in the reaction of the first invention may include, for example, an alkali metal hydride such as lithium hydride, sodium hydride, etc.; an alkaline earth metal hydride such as calcium hydride, etc.; an alkali metal alkoxide such as sodium methoxide, sodium ethoxide, sodium n-propoxide, sodium isopropoxide, sodium n-butoxide, sodium tert-butoxide, potassium methoxide, potassium ethoxide, potassium n-propoxide, potassium isopropoxide, potassium n-butoxide, potassium tert-butoxide, etc. (incidentally, these may be used as a corresponding alcohol solution); an alkali metal carbonate such as sodium carbonate, potassium carbonate, etc.; an alkali metal hydrogen carbonate such as sodium hydrogen carbonate, potassium hydrogen carbonate, etc.; an alkali metal hydroxide such as sodium hydroxide, potassium hydroxide, etc., preferably an alkali metal hydride, an alkali metal alkoxide, further preferably sodium hydride and/or sodium methoxide is/are used. Incidentally, these bases may be used alone or in combination of two or more in admixture.

An amount of the above-mentioned base is preferably 0.1 to 10 mol, further preferably 1 to 5 mol based on 1 mol of the 4-acyltetrahydropyran.

The reaction of the first invention is carried out in the presence or absence of a solvent. The solvent to be used is not specifically limited so long as it does not interfere the reaction, and there may be mentioned, for example, an aliphatic hydrocarbon such as n-pentane, n-hexane, n-heptane, i-heptane, n-octane, i-octane, cyclo-pentane, cyclohexane, methylcyclohexane, etc.; an aromatic hydrocarbon such as toluene, xylene, mesitylene, etc.; a halogenated aromatic hydrocarbon such as fluorobenzene, chlorobenzene, dichlorobenzene, etc.; an amide such as N,N-dimethylformamide, N,N-dimethylacetamide, N-methylpyrrolidone, etc.; a urea such as N,N'-dimethylimidazolidinone, etc.; a sulfoxide such as dimethyl sulfoxide, sulfolane, etc.; an ether such as diisopropyl ether, tetrahydropyran, dioxane, cyclopropyl methyl ether, etc.; an alcohol such as methanol, ethanol, isopropyl alcohol, t-butyl alcohol, etc.; a nitrile such as acetonitrile, propionitrile, butyronitrile, etc. Incidentally, these solvents may be used alone or in combination of two or more in admixture.

An amount of the above-mentioned solvent may be optionally adjusted depending on a degree of uniformity or condition of stirring of the reaction solution, and is preferably 0 to 100 ml, further preferably 0 to 50 ml based on 1 g of the 4-acyltetrahydropyran.

The reaction of the first invention can be carried out by the method in which, for example, a 4-acyltetrahydropyran, a carbonic acid diester and a base are mixed (if necessary, a solvent is also mixed), and these materials are reacted with stirring, etc. A temperature at that time is preferably 20 to 150° C., further preferably 35 to 130° C., and a reaction pressure is normal pressure or reduced pressure. Incidentally, it is desirable to carry out the reaction while an alcohol existing in the reaction system is distilling off.

After completion of the reaction, the final product, the alkyl 3-(4-tetrahydropyranyl)-3-oxopropanoate compound is isolated and purified by a general method, for example, neutralization, filtration, concentration, distillation, recrystallization, column chromatography, etc.

The 4-acyltetrahydropyran represented by the formula (2) to be used as a starting compound in the present invention can be prepared, for example, by the second invention which comprises subjecting a 4-acyl-4-alkoxycarbonyltetrahydropyran represented by the formula (4):

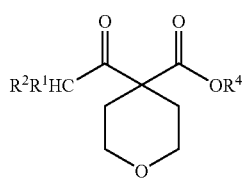

(4)

wherein $R^1$ and $R^2$ have the same meanings as defined above, and $R^4$ represents an alkyl group, to decarboxylation in the presence of an acid.

The 4-acyl-4-alkoxycarbonyltetrahydropyran to be used in the decarboxylation of the second invention is represented by the above-mentioned formula (4). In the formula (4), $R^1$ and $R^2$ have the same meanings as defined above. Also, $R^4$ is an alkyl group, and more specifically, there may be specifically mentioned, for example, a linear or branched alkyl group having 1 to 6 carbon atoms such as a methyl group, an ethyl group, a propyl group, a butyl group, a pentyl group, a hexyl group, etc. Incidentally, these groups contain various kinds of isomers.

The acid to be used in the decarboxylation of the second invention may include, for example, a carboxylic acid such as formic acid, acetic acid, trifluoroacetic acid, etc.; a sulfonic acid such as methanesulfonic acid, trifluoromethanesulfonic acid, benzenesulfonic acid, p-toluenesulfonic acid, etc.; a mineral acid such as hydrochloric acid, hydrobromic acid, hydroiodic acid, sulfuric acid, nitric acid, phosphoric acid, etc., preferably a mineral acid, further preferably hydrochloric acid, hydrobromic acid, hydroiodic acid, sulfuric acid, particularly preferably hydrochloric acid and/or sulfuric acid is/are used. Incidentally, these acids may be used alone or in combination of two or more in admixture.

An amount of the above-mentioned acid to be used is preferably 0.1 to 20 mol, more preferably 1 to 10 mol based on 1 mol of the 4-acyl-4-alkoxycarbonyltetrahydropyran.

The decarboxylation which is the second invention is preferably carried out in the presence of a solvent. The solvent to be used is not specifically limited so long as it does not inhibit the reaction, and there may be mentioned, for example, water; an alcohol such as methanol, ethanol, isopropyl alcohol, t-butyl alcohol, etc.; an amide such as N,N-dimethylformamide, N-methylpyrrolidone, etc.; a urea such as N,N'-dimethylimidazolidinone, etc.; an ether such as tetrahydrofuran, etc.; an aliphatic hydrocarbon such as hexane, heptane, etc.; an aromatic hydrocarbon such as toluene, xylene, etc. Incidentally, these solvents may be used alone or in combination of two or more in admixture.

An amount of the above-mentioned solvent may be optionally adjusted depending on a degree of uniformity or condition of stirring of the reaction solution, and is preferably 1 to 50 ml, more preferably 1 to 10 ml, further preferably 3 to 10 ml based on 1 g of the 4-acyl-4-alkoxycarbonyltetrahydropyran.

The decarboxylation which is the second invention can be carried out by a method, for example, in which a 4-acyl-4-alkoxycarbonyltetrahydropyran, an acid and a solvent are mixed, and they are reacted with stirring, etc. A reaction temperature at that time is preferably 50 to 150° C., more preferably 70 to 150° C., further preferably 90 to 140° C., and a reaction pressure is not specifically limited.

According to the decarboxylation which is the second invention, the 4-acyltetrahydropyran can be obtained, and the compound can be isolated and purified by a general method, for example, neutralization, extraction, filtration, concentration, distillation, recrystallization, crystallization, column chromatography, etc., after completion of the reaction.

The alkyl 3-(4-tetrahydropyranyl)-3-oxopropanoate compound represented by the formula (1) which is the third invention is a novel compound, and $R^1$, $R^2$ and $R^3$ are as defined above. Specific examples of such an alkyl 3-(4-tetrahydropyranyl)-3-oxopropanoate compound may include, for example, methyl 3-(4-tetrahydropyranyl)-3-oxopropanoate, methyl 3-(4-tetrahydropyranyl)-2-methyl-3-oxopropanoate, ethyl 3-(4-tetrahydropyranyl)-3-oxopropanoate, ethyl 3-(4-tetrahydropyranyl)-2-methyl-3-oxopropanoate, n-propyl 3-(4-tetrahydropyranyl)-3-oxopropanoate, n-propyl 3-(4-tetrahydropyranyl)-2-methyl-3-oxopropanoate, isopropyl 3-(4-tetrahydropyranyl)-3-oxopropanoate, isopropyl 3-(4-tetrahydropyranyl)-2-methyl-3-oxopropanoate, n-butyl 3-(4-tetrahydropyranyl)-3-oxopropanoate, n-butyl 3-(4-tetrahydropyranyl)-2-methyl-3-oxopropanoate, isobutyl 3-(4-tetrahydropyranyl)-3-oxopropanoate, isobutyl 3-(4-tetrahydropyranyl)-2-methyl-3-oxopropanoate, tert-butyl 3-(4-tetrahydropyranyl)-3-oxopropanoate, tert-butyl 3-(4-tetrahydropyranyl)-2-methyl-3-oxopropanoate, methyl 3-(4-tetrahydropyranyl)-2,2'-dimethyl-3-oxopropanoate, methyl 3-(4-tetrahydropyranyl)-2-ethyl-3-oxopropanoate, ethyl 3-(4-tetrahydropyranyl)-2-ethyl-3-oxopropanoate, n-propyl 3-(4-tetrahydropyranyl)-2-ethyl-3-oxopropanoate, isopropyl 3-(4-tetrahydropyranyl)-2-ethyl-3-oxopropanoate, n-butyl 3-(4-tetrahydropyranyl)-2-ethyl-3-oxopropanoate, isobutyl 3-(4-tetrahydropyranyl)-2-ethyl-3-oxopropanoate, tert-butyl 3-(4-tetrahydropyranyl)-2-ethyl-3-oxopropanoate, etc.

The fourth invention of the present invention is a 4-propionyl-4-alkoxycarbonyltetrahydropyran represented by the formula (5) in which $CHR^1R^2$ in the above-mentioned formula (4) is an ethyl group which is a novel compound, and $R^4$ is as defined above. Specific examples of such a 4-propionyl-4-alkoxycarbonyltetrahydropyran may include, for example, 4-propionyl-4-methoxycarbonyltetrahydropyran, 4-propionyl-4-ethoxycarbonyltetrahydropyran, 4-propionyl-4-n-propoxycarbonyltetrahydropyran, 4-propionyl-4-isopropoxycarbonyltetrahydropyran, 4-propionyl-4-n-butoxycarbonyltetrahydropyran, 4-propionyl-4-isobutoxycarbonyltetrahydropyran, 4-propionyl-4-tert-butoxycarbonyltetrahydropyran, etc.

EXAMPLES

Next, the present invention is explained more specifically by referring to Examples, but the scope of the present invention is not limited by these.

Reference Example 1

Synthesis of 4-acetyl-4-methoxycarbonyltetrahydropyran

In a flask made of glass having an inner volume of 1000 ml and equipped with a stirring device, a thermometer, a dropping funnel and a reflux condenser were charged 143 g (1.0 mol) of 2,2'-dichloroethyl ether, 276 g (2.0 mol) of anhydrous potassium carbonate, 10 g (0.06 mol) of potassium iodide and 600 ml of N,N-dimethylformamide, and the temperature of the mixture was raised to up to 80° C. with stirring. Then, 139 g (1.2 mol) of methyl 3-oxobutanoate was gently added dropwise to the mixture, and the mixture was reacted at the same temperature for 8 hours. After completion of the reaction, 1000 ml of water was added to the reaction mixture, and the resulting mixture was extracted three times with 600 ml of ethyl acetate. The organic layers were dried over magnesium sulfate, filtered, and the filtrate was distilled under reduced pressure (125 to 127° C., 1.3 kPa) to give 95 g (Isolation yield: 50%) of 4-acetyl-4-methoxycarbonyltetrahydropyran with a purity of 98% (areal percentage by gas chromatography) as a pale yellow liquid.

The physical properties of the 4-acetyl-4-methoxycarbonyltetrahydropyran were as follows.

CI-MS (m/e); 187 (M+1)

$^1$H-NMR (CDCl$_3$, δ (ppm)); 1.95 to 2.01 (2H, m), 2.13 to 2.18 (5H, m), 3.55 to 3.61 (2H, m), 3.73 to 3.79 (5H, m)

Example 1

Synthesis of 4-acetyltetrahydropyran

In a flask made of glass having an inner volume of 10 ml and equipped with a stirring device, a thermometer and a reflux condenser were charged 0.38 g (2.0 mmol) of 4-acetyl-4-methoxycarbonyltetrahydropyran with a purity of 99% and synthesized in the same manner as in Reference example 1 and 1.08 ml (10 mmol) of 9 mol/l sulfuric acid, and the mixture was reacted at 120° C. for 1.5 hours with stirring. After completion of the reaction, when the reaction mixture was analyzed by gas chromatography (Internal standard method), 0.25 g (Reaction yield: 96%) of 4-acetyltetrahydropyran was found to be formed.

Example 2

Synthesis of 4-acetyltetrahydropyran

In a flask made of glass having an inner volume of and equipped with a stirring device, a thermometer and a reflux condenser were charged 0.38 g (2.0 mmol) of 4-acetyl-4-methoxycarbonyltetrahydropyran with a purity of 99% and synthesized in the same manner as in Reference example 1 and 2.52 ml (10 mmol) of 4 mol/l hydrochloric acid, and the mixture was reacted at 120° C. for 4 hours with stirring. After completion of the reaction, when the reaction mixture was analyzed by gas chromatography (Internal standard method), 0.23 g (Reaction yield: 90%) of 4-acetyltetrahydropyran was found to be formed.

Example 3

Synthesis of 4-acetyltetrahydropyran

In a flask made of glass having an inner volume of 10 ml and equipped with a stirring device, a thermometer and a reflux condenser were charged 0.38 g (2.0 mmol) of 4-acetyl-4-methoxycarbonyltetrahydropyran with a purity of 99% and synthesized in the same manner as in Reference example 1 and 1.70 g (10 mmol) of 47% hydrobromic acid, and the mixture was reacted at 120° C. for 1 hour with stirring. After completion of the reaction, when the reaction mixture was analyzed by gas chromatography (Internal standard method), 0.17 g (Reaction yield: 65%) of 4-acetyltetrahydropyran was found to be formed.

Reference Example 2

Preparation Method of 4-acetyltetrahydropyran

In a flask made of glass having an inner volume of 10 ml and equipped with a stirring device, a thermometer, a dropping funnel and a reflux condenser were charged 202 g (1.0 mol) of 4-acetyl-4-methoxycarbonyltetrahydropyran with a purity of 95% and synthesized in the same manner as in Reference example 1 and 720 ml of methanol, and the temperature of the mixture was raised to 35° C. with stirring. Then, to the mixture was gently added dropwise a mixed solution comprising 201 g (2.0 mol) of 35% by weight aqueous hydrogen peroxide solution and 91 ml (0.73 mol) of 8 mol/l aqueous sodium hydroxide solution, and the mixture was reacted at 40° C. for 5 hours with stirring. After completion of the reaction, to the resulting reaction mixture was added a saturated aqueous sodium sulfate solution to decompose the remaining hydrogen peroxide, then, the mixture was concentrated under reduced pressure, and the concentrate was extracted three times with 500 ml of ethyl acetate. The organic layer was distilled under reduced pressure (90 to 92° C., 2.0 kPa) to give 113 g (Isolation yield: 85%) of 4-acetyltetrahydropyran with a purity of 99% (areal percentage by gas chromatography) as a colorless liquid.

Physical properties of the 4-acetyltetrahydropyran are as follows.

CI-MS (m/e); 129 (M+1)

$^1$H-NMR (CDCl$_3$, δ (ppm)); 1.60 to 1.82 (4H, m), 2.16 (3H, s), 2.50 to 2.61 (1H, m), 3.39 to 3.47 (2H, m), 3.96 to 4.02 (2H, m)

Example 4

Synthesis of methyl 3-(4-tetrahydropyranyl)-3-oxopropanoate

In a flask made of glass having an inner volume of 500 ml and equipped with a stirring device, a thermometer, a dropping funnel and a distillation device were charged 35.0 g (273 mmol) of 4-acetyltetrahydropyran synthesized in the same manner as in Reference example 2, 280.0 g (3.1 mol) of dimethyl carbonate and 16.3 g (302 mmol) of sodium methoxide, and the mixture was reacted at 80 to 85° C. for 2 hours with distilling by-producing methanol off. After completion of the reaction, the reaction mixture was cooled to 5 to 10° C., and to the reaction mixture were added 175 ml of toluene, 55 ml (330 mmol) of 6 mol/l hydrochloric acid and 35 ml of water in this order. After the organic layer was separated, the aqueous layer was extracted twice with 70 ml of toluene. The organic layer was concentrated under reduced pressure, and the concentrate was purified by silica gel column chromatography (Fluent; hexane/ethyl acetate=1/1 (volume ratio)) to give 40.9 g (Isolation yield: 76%) of methyl 3-(4-tetrahydropyranyl)-3-oxopropanoate with a purity of 93.9% (analytical value by differential diffractometry) as a colorless liquid.

Methyl 3-(4-tetrahydropyranyl)-3-oxopropanoate is a novel compound shown by the following physical properties.

CI-MS (m/e); 187 (M+1)

$^1$H-NMR (CDCl$_3$, δ (ppm)); 1.68 to 1.82 (4H, m), 2.66 to 2.72 (1H, m), 3.38 to 3.47 (2H, m), 3.51 (2H, s), 3.75 (3H, s), 3.97 to 4.04 (2H, m)

Reference Example 3

Synthesis of 4-propionyl-4-methoxycarbonyltetrahydropyran

In a flask made of glass having an inner volume of 200 ml and equipped with a stirring device, a thermometer, a dropping funnel and a reflux condenser were charged 13.0 g (0.09 mol) of 2,2'-dichloroethyl ether, 35.9 g (0.26 mol) of anhydrous potassium carbonate, 1.3 g (7.8 mmol) of potassium iodide and 80 ml of N,N-dimethylformamide, and the temperature of the mixture was raised to 80° C. with stirring. Then, 20.0 g (0.15 mol) of methyl 3-oxopentanoate was gently added dropwise to the mixture, and the mixture was reacted at the same temperature for 7 hours. After completion of the reaction, to the reaction mixture were added 200 ml of water and 32.3 g (0.31 mol) of conc. hydrochloric acid to adjust a pH of the mixture to 4.5. Said reaction mixture was extracted three times with 200 ml of ethyl acetate. The organic layer was dried over magnesium sulfate, filtered, and the filtrate was concentrated under reduced pressure. The obtained concentrate was purified by silica gel column chromatography (Eluent; hexane/ethyl acetate=3/1 (volume ratio)) to give 10.1 g (Isolation yield: 55%) of 4-propionyl-4-methoxycarbonyltetrahydropyran as a pale yellow liquid.

Physical properties of the 4-propionyl-4-methoxycarbonyltetrahydropyran are as follows.

CI-MS (m/e); 201 (M+1)

$^1$H-NMR (CDCl$_3$, δ (ppm)); 1.03 to 1.07 (3H, t), 1.95 to 2.19 (4H, m), 2.44 to 2.51 (2H, q), 3.48 to 3.80 (4H, m), 3.76 (3H, s)

Example 5

Preparation Method of 4-propionyltetrahydropyran

In a flask made of glass having an inner volume of 10 ml and equipped with a stirring device, a thermometer, a dropping funnel and a reflux condenser were charged 4.8 g (24 mmol) of 4-propionyl-4-methoxycarbonyltetrahydropyran synthesized in Example 2, 30 ml of water and 9.0 g of conc. sulfuric acid, and the mixture was reacted at 100° C. for 10 hours with stirring. After completion of the reaction, to the resulting reaction mixture was added 16.5 g of 50% by weight aqueous sodium hydroxide solution to adjust a pH of the mixture to 4.0. Said reaction mixture was extracted three times with 50 ml of ethyl acetate, and the organic layer was separated and concentrated under reduced pressure. The obtained concentrate was purified by silica gel column chromatography (Eluent; hexane/ethyl acetate=3/1 (volume ratio)) to give 2.58 g (Isolation yield: 76%) of 4-propionyltetrahydropyran as a pale yellow liquid.

Physical properties of the 4-propionyltetrahydropyran are as follows.

CI-MS (m/e); 143 (M+1)

$^1$H-NMR (CDCl$_3$, δ (ppm)); 1.03 to 1.08 (3H, t), 1.68 to 1.76 (4H, m), 2.45 to 2.52 (2H, q), 2.53 to 2.62 (1H, m), 3.39 to 3.43 (2H, m), 3.96 to 4.02 (2H, m)

Example 6

Synthesis of methyl 3-4-tetrahydropyranyl-2-methyl-3-oxopropanoate

In a flask made of glass having an inner volume of 100 ml and equipped with a stirring device, a thermometer, a dropping funnel and a distillation device were charged 1.28 g (9 mmol) of 4-propionyltetrahydropyran synthesized in the same manner as in Example 5, 16.0 g (180 mmol) of dimethyl carbonate and 1.2 g (22 mmol) of sodium methoxide, and the mixture was reacted at 80 to 85° C. for 2 hours with distilling by-producing methanol off. After completion of the reaction, the reaction mixture was cooled to 5 to 10° C., to the reaction mixture were added 50 ml of ethyl acetate, 3.4 g (24 mmol) of 6 mol/l hydrochloric acid and 15 ml of water in this order. After the organic layer was separated, the aqueous layer was extracted twice with 50 ml of ethyl acetate. The organic layer was concentrated under reduced pressure, and the concentrate was purified by silica gel column chromatography (Eluent; hexane/ethyl acetate=3/1 (volume ratio)) to give 0.60 g (Isolation yield: 33%) of methyl 3-(4-tetrahydropyranyl)-2-methyl-3-oxopropanoate as a colorless liquid.

Methyl 3-(4-tetrahydropyranyl)-2-methyl-3-oxopropanoate is a novel compound shown by the following physical properties.

CI-MS (m/e); 201 (M+1)

$^1$H-NMR (CDCl$_3$, δ (ppm)); 1.32 to 1.36 (3H, d), 1.68 to 1.81 (4H, m), 2.74 to 2.84 (1H, m), 3.38 to 3.48 (2H, m), 3.66 to 3.72 (1H, q), 3.73 (3H, s), 3.97 to 4.03 (2H, m)

Example 7

Synthesis of ethyl 3-4-tetrahydropyranyl-3-oxopropanoate

In an apparatus made of glass having an inner volume of 100 ml and equipped with a stirring device, a thermometer, a reflux condenser and a dropping funnel were charged 4.56 g (31 mmol) of diethyl carbonate and 3.98 g (58 mmol) of sodium ethoxide, and the temperature of the liquid was raised to 85° C. Then, 5.0 g (39 mmol) of 4-acetyltetrahydropyran was gently added dropwise to the mixture. Further, 4.56 g (31 mmol) of diethyl carbonate was added to the mixture, and the mixture was reacted at 80 to 90° C. for 1 hour. After completion of the reaction, 5 ml of 2-butanol was added to the mixture at the same temperature, and after cooling to room temperature, 5 ml of ethanol was added to the mixture (this is called to as the reaction mixture A).

In an apparatus made of glass having an inner volume of 100 ml and equipped with a stirring device, a thermometer, a reflux condenser and a dropping funnel were charged 4.22 g (70 mmol) of acetic acid and 10 ml of saturated brine and to the mixed solution was gently added dropwise the reaction mixture A with maintaining the liquid temperature to 0 to 10° C. Then, after the temperature was raised to room temperature, 10 ml of ethyl acetate and 10 ml of water were added and the liquids were separated. The resulting organic layer was concentrated under reduced pressure, and the concentrate was purified by silica gel column chromatography (hexane:ethyl acetate=10:1→10:2) to give 1.0 g (Isolation yield: 13%) of ethyl 3-(4-tetrahydropyranyl)-3-oxopropanoate as a colorless liquid.

Ethyl 3-(4-tetrahydropyranyl)-3-oxopropanoate is a novel compound shown by the following physical properties.

CI-MS (m/e); 201 (M+1)
$^1$H-NMR (CDCl$_3$, δ (ppm)); 1.28 (3H, t, J=7.1 Hz), 1.68 to 1.83 (4H, m), 2.66 to 2.77 (1H, m), 3.39 to 3.47 (2H, m), 3.50 (2H, s), 3.97 to 4.04 (2H, m), 4.20 (2H, q, J=7.1 Hz)

UTILIZABILITY IN INDUSTRY

The present invention relates to a process for preparing an alkyl 3-(4-tetrahydropyranyl)-3-oxopropanoate compound from 4-acyltetrahydropyran. The alkyl 3-(4-tetra-hydropyranyl)-3-oxopropanoate compound is a useful compound as a starting material or a synthetic intermediate of medicines, agricultural chemicals, etc.

The present invention is also relates to a process for preparing a 4-acyltetrahydropyran from a 4-acyl-4-alkoxycarbonyltetrahydropyran. The 4-acyltetrahydropyran is a useful compound as a starting material or a synthetic intermediate of medicines, agricultural chemicals, etc.

The invention claimed is:

1. A process for preparing 4-acyltetrahydropyran represented by the formula (2):

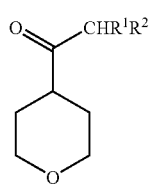

(2)

wherein R$^1$ and R$^2$ may be the same or different from each other, and represent a group which does not participate in the reaction, and R$^1$ and R$^2$ may be bonded to form a ring, and the ring may contain a hetero atom(s), which comprises subjecting 4-acyl-4-alkoxycarbonyltetrahydropyran represented by the formula (4):

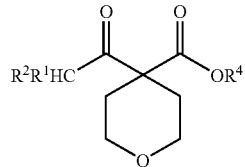

(4)

wherein R$^1$ and R$^2$ have the same meanings as defined above, and R$^4$ represents an alkyl group, to decarboxylation in the presence of a mineral acid.

2. The process according to claim 1, wherein the mineral acid is hydrochloric acid or sulfuric acid.

3. The process according to claim 1, wherein the decarboxylation is carried out at a temperature of 90 to 140° C.

4. The process according to claim 1, wherein R$^1$ and R$^2$ may be the same or different from each other, and each represents one selected from the group consisting of a hydrogen atom; a methyl group, an ethyl group, a propyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group; a benzyl group, a phenethyl group; a phenyl group, a tolyl group; a methoxy group, an ethoxy group, a propoxy group; a benzyloxy group, a phenethyloxy group; a phenoxy group; a formyl group, an acetyl group, a propionyl group, a benzoyl group; a formyloxy group, an acetoxy group, a benzoyloxy group; a fluorine atom, a chlorine atom, a bromine atom and an iodine atom.

5. The process according to claim 1, wherein R$^4$ is a linear or branched alkyl group having 1 to 6 carbon atoms.

6. The process according to claim 1, wherein the compound of the formula (4) is selected from the group consisting of 4-acetyl-4-methoxycarbonyltetrahydropyran and 4-propionyl-4-methoxycarbonyltetrahydropyran.

7. The process according to claim 1, wherein the compound of the formula (2) is selected from the group consisting of 4-acetyltetrahydropyran and 4-propionyltetrahydropyran.

8. The process according to claim 1, wherein an amount of the mineral acid is 0.1 to 20 mol based on 1 mol of the 4-acyl-4-alkoxycarbonyltetrahydropyran.

9. The process according to claim 1, wherein an amount of the mineral acid is 1 to 10 mol based on 1 mol of the 4-acyl-4-alkoxycarbonyltetrahydropyran.

10. The process according to claim 1, wherein the reaction is carried out in the presence of a solvent.

11. The process according to claim 10, wherein the solvent is selected from the group consisting of water; an alcohol; an amide; an urea; an ether; an aliphatic hydrocarbon; and an aromatic hydrocarbon.

12. The process according to claim 10, wherein the solvent is selected from the group consisting of water; methanol, ethanol, isopropyl alcohol, t-butyl alcohol, N,N-dimethylformamide, N-methylpyrrolidone, N,N'-dimethylimidazolidinone, tetrahydrofuran, hexane, heptane, toluene and xylene.

13. The process according to claim 10, wherein an amount of the solvent is 3 to 10 ml based on 1 g of the 4-acyl-4-alkoxycarbonyltetrahydropyran.

* * * * *